(12) United States Patent
Suzuki et al.

(10) Patent No.: US 8,273,781 B2
(45) Date of Patent: Sep. 25, 2012

(54) PROCESS FOR PREPARATION OF 1-ALKYL-5-BENZOYL-1H-TETRAZOLE DERIVATIVES

(75) Inventors: Tatsumi Suzuki, Odawara (JP); Tadashi Sugiura, Hiratsuka (JP); Yoshikazu Ito, Naka-gun (JP)

(73) Assignee: Nippon Soda Co., Ltd., Tokyo (JP)

( * ) Notice: Subject to any disclaimer, the term of this patent is extended or adjusted under 35 U.S.C. 154(b) by 0 days.

(21) Appl. No.: 13/255,345

(22) PCT Filed: Mar. 8, 2010

(86) PCT No.: PCT/JP2010/001597
§ 371 (c)(1),
(2), (4) Date: Sep. 8, 2011

(87) PCT Pub. No.: WO2010/103783
PCT Pub. Date: Sep. 16, 2010

(65) Prior Publication Data
US 2012/0004420 A1 Jan. 5, 2012

(30) Foreign Application Priority Data
Mar. 11, 2009 (JP) ................. 2009-057874

(51) Int. Cl.
*A61K 31/41* (2006.01)
*C07D 257/04* (2006.01)
(52) U.S. Cl. ........................ 514/381; 548/250
(58) Field of Classification Search .................. 514/381; 548/250
See application file for complete search history.

(56) References Cited

U.S. PATENT DOCUMENTS
3,962,272 A 6/1976 Katner

FOREIGN PATENT DOCUMENTS

| EP | 1 426 371 | 6/2004 |
|---|---|---|
| GB | 2 200 911 | 8/1988 |
| JP | 49-075580 | 7/1974 |
| JP | 2002-532466 | 10/2002 |
| JP | 2004-131392 | 4/2004 |
| WO | 00/35868 | 6/2002 |
| WO | 03/016303 | 2/2003 |
| WO | WO 03/016303 A1 * | 2/2003 |
| WO | 2009/090237 | 7/2009 |

OTHER PUBLICATIONS

R. Raap "Reactions of 1-Substituted 5-Tetrazolyllithium Compounds; Preparation of 5-Substituted 1-Methyltetrazoles" Canadian Journal of Chemistry, 2139-2142, vol. 49, 1971.

Ivar Ugi and Uwe Fetzer, Isonitrile. III. The addition of carboxylic acid chlorides to isonitrile, Chemische Berichte, 1961, vol. 94, p. 1116-1121.
International Search Report dated PCT/JP2010/001597, dated Jun. 1, 2010.
European Search Report issued for EP application No. 10750541.4, dated Jul. 6, 2012, 10 pages.
Ugi, Ivar, et al., "Die Addition von Carbonsäurechnloriden an Isonitrile", Chemische Berichte, 1961, vol. 94, pp. 1116-1121.
Sustmann, R., et al., "Carbonsaure-halogenid-imide, -hydroximide, -hydrazonide bzw. 1-Diazo-1-halogen-alkane", Methoden der Organischen Chemie (Houben-Weyl), 1985, vol. E5, pp. 628-631.
Meier, H.R., at al., "Tetrazole", Methoden der Organischen Chemie (Houben-Weyl) Hetarene III/Part 4, 1994, vol. E8d, pp. 700-703.

* cited by examiner

*Primary Examiner* — Susannah Chung
(74) *Attorney, Agent, or Firm* — Kenyon & Kenyon LLP

(57) ABSTRACT

The present invention provides a process for preparation of 1-alkyl-5-benzoyl-1H-tetrazole derivative including a step 1 of reacting a ketoamide derivative represented by formula (I) (in formula (I), A represents a halogen atom or the like; n represents an integer of 0 to 5; Y represents an alkyl group) with a halogenating agent to obtain an imidoyl halide derivative represented by formula (II) (in formula (II), A, n and Y are as defined above; X represents a halogen atom); and a step 2 of reacting the imidoyl halide derivative represented by formula (II) with an azide represented by formula (III) (in formula (III), M represents an alkali metal or the like; m represents 1 or 2) to obtain a 1-alkyl-5-benzoyl-1H-tetrazole derivative represented by formula (IV) (in formula (IV), A, n and Y are as defined above).

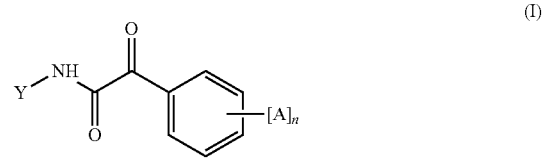

(I)

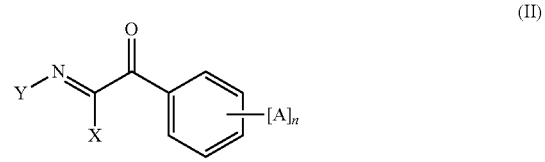

(II)

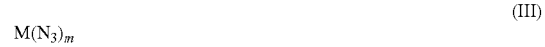

(III)

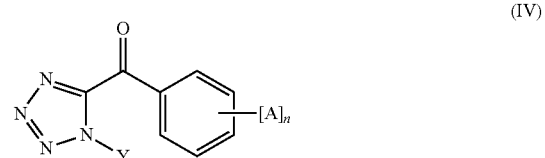

(IV)

5 Claims, No Drawings

PROCESS FOR PREPARATION OF 1-ALKYL-5-BENZOYL-1H-TETRAZOLE DERIVATIVES

TECHNICAL FIELD

The present invention relates to a process for preparation of 1-alkyl-5-benzoyl-1H-terazole derivatives. More specifically, the present invention relates to a process for preparation of 1-alkyl-5-benzoyl-1H-terazole derivatives, in which as a starting material thereof a relatively easily-producible and easily-available ketoamide derivative represented by formula (I) is used:

[Chemical formula 1]

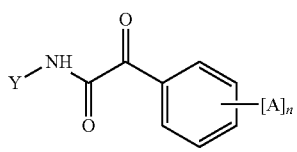

(I)

(In formula, A represents a halogen atom, alkyl group, haloalkyl group, alkoxy group, haloalkoxy group, alkyl sulfonyl group, an optionally substituted aryl group, cyano group or nitro group; n represents an integer of 0 to 5 (when n is 2 or more, plural A may be the same or different from each other); Y represents an alkyl group).

Priority is claimed on Japanese Patent Application No. 2009-057874, filed Mar. 11, 2009, the content of which is incorporated herein by reference.

BACKGROUND ART

To date, a number of disease control agents for use with agricultural and horticultural crops have been proposed. For example, Patent document 1 discloses a tetrazolyl oxime derivative represented by formula (1-a) having excellent drug efficacy in useful plants, and suggests using the compound as a plant disease control agent.

[Chemical formula 2]

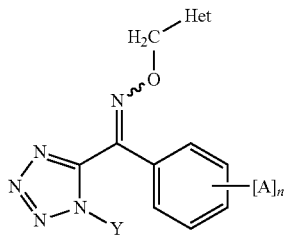

(1-a)

In formula (1-a), A represents a halogen atom, alkyl group, alkoxy group, methane sulfonyl group, trifluoromethyl group, aryl group, cyano group or nitro group; n represents an integer of 0 to 5; Y represents an alkyl group; Het represents a substituted pyridyl group or a substituted thiazolyl group.

[Chemical formula 3]

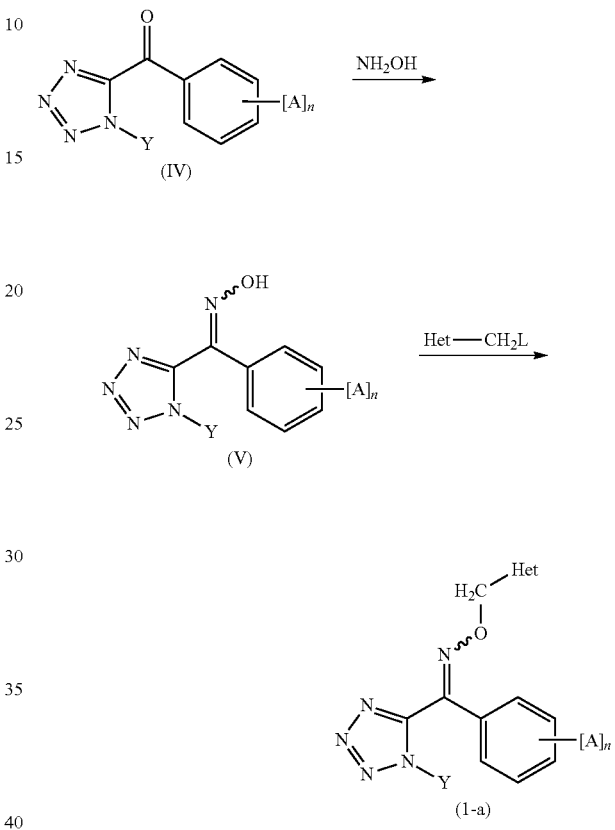

This tetrazolyl oxime derivative represented by formula (1-a) can be produced by reacting a 1-alkyl-5-benzoyl-1H-tetrazole derivative with a hydroxylamine to obtain a tetrazolyl hydroxyimino derivative represented by formula (V), followed by reacting the obtained tetrazolyl hydroxyimino derivative with a Het-CH2L (provided that L represents a chlorine atom, bromine atom or iodine atom) in the presence of a base (for example, sodium hydride, sodium hydroxide, potassium hydroxide, sodium carbonate, potassium carbonate, cesium carbonate, triethylamine, pyridine, N,N-dimethyl aminopyridine or the like).

[Chemical formula 4]

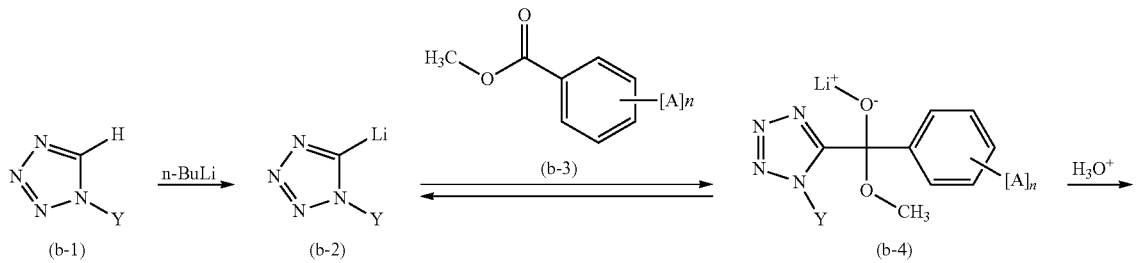

The 1-alkyl-5-benzoyl-1H-tetrazole derivative represented by formula (IV), which is used as a raw material of this reaction, can be obtained by a method described in Non-patent document 1. Namely, the 1-alkyl-5-benzoyl-1H-tetrazole derivative represented by formula (IV) may be obtained by reacting a tetrazole derivative represented by formula (b-1) with an organic lithium compound to obtain a derivative represented by formula (b-2), and reacting the obtained derivative with an ester compound represented by formula (b-3) to obtain a derivative represented by formula (b-4), followed by causing an acid to act upon the obtained derivative.

PRIOR ART LITERATURE

Patent Document
Patent document 1: WO 2003/01633
Non-Patent Document
Non-patent document 1: R. RAAP "Reactions of 1-Substituted 5-Tetrazolyllithium Compounds; Preparation of 5-Substituted 1-Methyltetrazoles" Canadian Journal of Chemistry, 2139-2142, Vol. 49, 1971

DISCLOSURE OF INVENTION

Problems to be Solved by the Invention

However, in the process for preparation of 1-alkyl-5-benzoyl-1H-tetrazole derivative represented by formula (IV) described in Non-patent document 1, the raw material is restricted. Therefore, the objective of the present invention is to provide a process for preparation of 1-alkyl-5-benzoyl-1H-tetrazole derivative using other raw materials as a starting material.

Means for Solving the Problems

As a result of conducting extensive studies to achieve the above objective, the inventors of the present invention discovered that a 1-alkyl-5-benzoyl-1H-tetrazole derivative can be easily obtained by reacting as a starting material a ketoamide derivative represented by formula (I), which is relatively easy to produce and access, with a halogenating agent to obtain an imidoyl halide derivative represented by formula (II), followed by reacting the obtained imidoyl halide derivative with an azide represented by formula (III). The present invention was achieved on the basis of this perception.

Namely, the present invention is a process for preparation of 1-alkyl-5-benzoyl-1H-tetrazole derivative including: a step 1 of reacting a ketoamide derivative represented by formula (I) with a halogenating agent to obtain an imidoyl halide derivative represented by formula (II), and a step 2 of reacting the obtained imidoyl halide derivative represented by formula (II) with an azide represented by formula (III) to obtain a 1-alkyl-5-benzoyl-1H-tetrazole derivative represented by formula (IV).

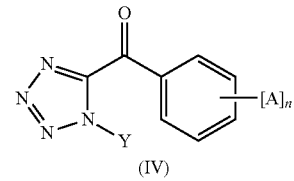

(IV)

[Chemical formula 5]

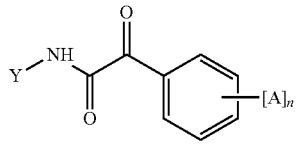

(I)

(in formula (I), A represents a halogen atom, alkyl group, haloalkyl group, alkoxy group, haloalkoxy group, alkyl sulfonyl group, optionally substituted aryl group, cyano group or nitro group; n represents an integer of 0 to 5 (when n is 2 or more, plural A may be the same or different from each other); Y represents an alkyl group).

[Chemical formula 6]

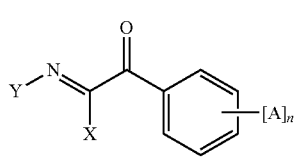

(II)

(in formula (II), A, n and Y are as defined above. X represents a halogen atom).

[Chemical formula 7]

$$M(N_3)_m \quad (III)$$

(in formula (III), M represents an alkali metal or alkali earth metal; m represents 1 or 2).

[Chemical formula 8]

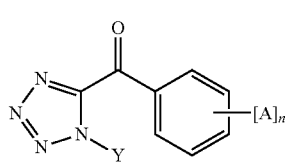

(IV)

(in formula (IV), A, n and Y are as defined above).

In the step 1, the halogenating agent is preferably at least one selected from the group consisting of phosgene, oxalyl chloride, thionyl chloride and phosphorus oxychloride.

In the step 2, the azide represented by formula (III) is preferably a sodium azide.

In the step 1, chloroform, methylene chloride or benzene is preferably used as a solvent.

In addition, the present invention is a process for preparation of tetrazolyl hydroxyimino derivative including causing a hydroxylamine or salt thereof to act upon the 1-alkyl-5- benzoyl-1H-tetrazole derivative obtained by the above-described method to obtain a tetrazolyl hydroxyimino derivative represented by formula (V):

[Chemical formula 9]

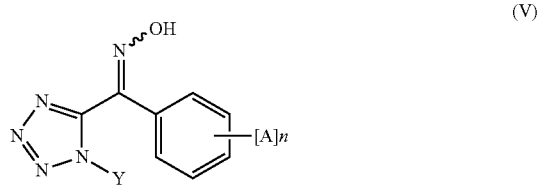

(in formula (V), A, n and Y are as defined above).

Effects of the Invention

According to the present invention, a ketoamide derivative represented by formula (I), which is relatively easy to produce and access, can be used as a starting material. A 1-alkyl-5-benzoyl-1H-tetrazole derivative represented by formula (IV) can be easily obtained by reacting the ketoamide derivative represented by formula (I) with a halogenating agent to obtain an imidoyl halide derivative represented by formula (II), followed by reacting the obtained imidoyl halide derivative with an azide represented by formula (III). In addition, a tetrazolyl hydroxyimino derivative can be easily obtained by reacting the 1-alkyl-5-benzoyl-1H-tetrazole derivative represented by formula (IV) with a hydroxylamine or salt thereof.

The 1-alkyl-5-benzoyl-1H-tetrazole derivative represented by formula (IV) and the tetrazolyl hydroxyimino derivative represented by formula (V) are useful as an intermediate for producing a plant disease control agent.

For example, the tetrazolyl oxime derivative represented by the aforementioned formula (1-a), which has a superior plant disease control effect, can be produced by reacting the 1-alkyl-5-benzoyl-1H-tetrazole derivative represented by formula (IV) with a hydroxylamine to obtain the tetrazolyl hydroxyimino derivative represented by formula (V), followed by reacting the obtained tetrazolyl hydroxyimino derivative with a Het-CH2L (provided that L represents a chlorine atom, bromine atom or iodine atom) in the presence of a base.

BEST MODE FOR CARRYING OUT THE INVENTION

The process for preparation of 1-alkyl-5-benzoyl-1H-tetrazole derivative represented by formula (IV) of the present invention includes a step 1 of reacting the ketoamide derivative represented by formula (I) with a halogenating agent to obtain an imidoyl halide derivative represented by formula (II), and a step 2 of reacting the imidoyl halide derivative represented by formula (II) with an azide to obtain a 1-alkyl-5-benzoyl-1H-tetrazole derivative represented by formula (IV).

I. Production of Imidoyl Halide Derivative Represented by Formula (II)

The ketoamide derivative represented by formula (I) can be obtained by amidating an α-oxocarboxylic acid ester represented by formula (O) (in formula (O), R represents an alkyl group or the like) or the like using YNH2. In addition, the ketoamide derivative represented by formula (I) can also be obtained according to a process for preparation of α-ketoamide derivative described in Japanese patent application publication 2002-532466.

In addition, the α-oxocarboxylic acid ester represented by formula (O) can be easily produced from an α-oxocarboxylic acid or salt thereof, an α-hydroxycarboxylic acid or the like, which have a corresponding structure to the α-oxocarboxylic acid ester.

[Chemical formula 10]

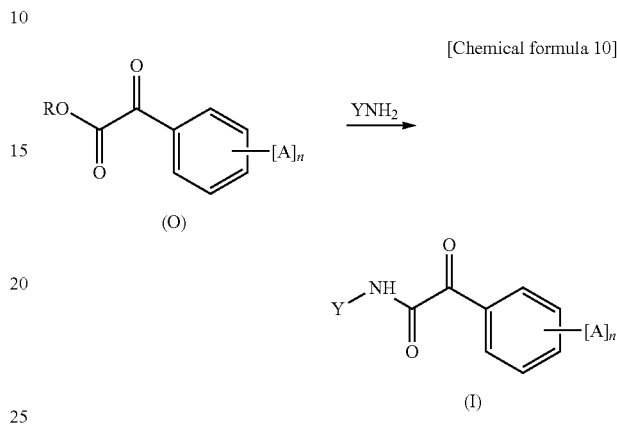

In formula (I), A represents a halogen atom, alkyl group, haloalkyl group, alkoxy group, haloalkoxy group, alkyl sulfonyl group, optionally substituted aryl group, cyano group or nitro group.

Examples of the halogen atom include a fluorine atom, chlorine atom, bromine atom and iodine atom.

Examples of the alkyl group include a methyl group, ethyl group, n-propyl group, i-propyl group, n-butyl group, i-butyl group, s-butyl group, t-butyl group, n-pentyl group, n-hexyl group and the like. The number of carbon atoms constituting the alkyl group is preferably 1 to 8.

Examples of the haloalkyl group include a fluoromethyl group, chloromethyl group, bromomethyl group, difluoromethyl group, dichloromethyl group, trifluoromethyl group, trichloromethyl group, trifluoroethyl group, pentafluoroethyl group, 3,3,3,2,2-pentafluoropropyl group, 2,2,2-trifluoro-1-trifluoromethyl ethyl group and the like.

The number of carbon atoms constituting the haloalkyl group is preferably 1 to 8.

Examples of the alkoxy group include a methoxy group, ethoxy group, n-propoxy group, i-propoxy group, n-butoxy group, i-butoxy group, s-butoxy group, t-butoxy group, n-hexyloxy group and the like. The number of carbon atoms constituting the alkoxy group is preferably 1 to 8.

Examples of the haloalkoxy group include a 2-chloro-n-propoxy group, 2,3-dichlorobutoxy group, trifluoromethoxy group and the like. The number of carbon atoms constituting the haloalkoxy group is preferably 1 to 8.

Examples of the alkyl sulfonyl group, methyl sulfonyl group, ethyl sulfonyl group, n-propyl sulfonyl group, i-propyl sulfonyl group, t-butyl sulfonyl group and the like. The number of carbon atoms constituting the alkyl sulfonyl group is preferably 1 to 8.

Aryl group means a monocyclic or polycyclic group. In addition, if the polycyclic aryl group has at least one aromatic ring, the other rings may be a saturated ring, unsaturated ring or aromatic ring. Among these aryl groups, a C6-10 aryl group is preferable.

Examples of the unsubstituted aryl group include a phenyl group, 1-naphthyl group, 2-naphthyl group, azulenyl group, indanyl group, tetralinyl and the like.

The "substituent" of the substituted aryl group is not particularly limited as long as it is chemically acceptable. Specifically, the following substituents may be exemplified.

(1) halogen atoms such as a fluorine atom, chlorine atom, bromine atom or iodine atom; (2) alkyl groups such as a methyl group, ethyl group, n-propyl group, i-propyl group, n-butyl group, s-butyl group, i-butyl group, t-butyl group, n-pentyl group or n-hexyl group; (3) cycloalkyl groups such as a cyclopropyl group, cyclobutyl group, cyclopentyl group, cyclohexyl group or cycloheptyl group; (4) alkoxy groups such as a methoxy group, ethoxy group, n-propoxy group, isopropoxy group, n-butoxy group, i-butoxy group, s-butoxy group or t-butoxy group; (5) alkenyl groups such as a vinyl group, 1-propenyl group, 2-propenyl group, 1-butenyl group, 2-butenyl group, 3-butenyl group, 1-methyl-2-propenyl group, 2-methyl-2-propenyl group, 1-pentenyl group, 2-pentenyl group, 3-pentenyl group, 4-pentenyl group, 1-methyl-2-butenyl group, 2-methyl-2-butenyl group, 1-hexenyl group, 2-hexenyl group, 3-hexenyl group, 4-hexenyl group or 5-hexenyl group;

(6) cycloalkenyl groups such as a 2-cyclopropenyl group, 2-cyclopentenyl group, 3-cyclohexenyl group or 4-cyclooctenyl group; (7) alkenyloxy groups such as a vinyloxy group, allyloxy group, 1-propenyloxy group or 2-butenyloxy group; (8) alkynyl groups such as an ethynyl group, 1-propynyl group, 2-propynyl group, 1-butynyl group, 2-butynyl group, 3-butynyl group, 1-methyl-2-propynyl group, 2-methyl-3-butynyl group, 1-pentynyl group, 2-pentynyl group, 3-pentynyl group, 4-pentynyl group, 1-methyl-2-butynyl group, 2-methyl-3-pentynyl group, 1-hexynyl group or 1,1-dimethyl-2-butynyl group; (9) alkynyloxy groups such as an ethynyloxy group or propargyloxy group; (10) aryl groups such as a phenyl group, 1-napthyl group or 2-naphthyl group;

(11) aryloxy groups such as a phenoxy group or 1-naphthoxy group; (12) aralkyl groups such as a benzyl group or phenethyl group; (13) aralkyloxy groups such as a benzyloxy group or phenethyloxy group; (14) acyl groups such as a formyl group, acetyl group, propionyl group, benzoyl group, cyclohexylcarbonyl group, phthaloyl group; (15) alkoxycarbonyl groups, such as a methoxycarbonyl group, ethoxycarbonyl group, n-propoxycarbonyl group, i-propoxycarbonyl group, n-butoxycarbonyl group, t-butoxycarbonyl group, (16) carboxyl groups; (17) hydroxyl groups; (18) haloalkyl groups such as a chloromethyl group, chloroethyl group, 1,2-dichloro-n-propyl group, 1-fluoro-n-butyl group or per-fluoro-n-pentyl group; (19) haloalkoxy groups such as 2-chloro-n-propoxy group, or 2,3-dichlorobutoxy group, trifluoromethoxy group; (20) haloalkenyl groups such as a 2-chloro-1-propenyl group or 2-fluoro-1-butenyl group; (21) haloalkynyl groups such as a 4,4-dichloro-1-butynyl group, 4-fluoro-1-pentynyl group or 5-bromo-2-pentynyl group;

(22) haloalkenyloxy groups such as a 2-chloro-1-propenyloxy group or 3-bromo-2-butenyloxy group; (23) haloalkynyl groups such as a 3-chloro-propargyl group or 3-iodo-propargyl group; (24) haloalkynyloxy groups such as a 3-chloro-propargyloxy group or 3-iodo-propargyloxy group; (25) haloaryl groups such as a 4-chlorophenyl group, 4-fluorophenyl group or 2,4-dichlorophenyl group; (26) haloaryloxy groups such as a 4-fluorophenoxy group or 4-chloro-1-naphthoxy group; (27) halogen-substituted acyl groups such as a chloroacetyl group, trifluoroacetyl group, trichloroacetyl group or 4-chlorobenzoyl group; (28) alkoxyalkyl groups such as a methoxymethyl group, ethoxymethyl group, 1-ethoxyethyl group or 2-ethoxyethyl group; (29) alkoxyalkoxy groups such as a methoxymethoxy group, ethoxymethoxy group, 1-ethoxyethoxy group or 2-ethoxyethoxy group; (30) cyano groups;

(31) isocyano groups; (32) nitro groups; (33) isocyanato groups; (34) cyanato groups; (35) amino groups ($NH_2$); (36) alkylamino groups such as a methylamino group, dimethylamino group or diethylamino group; (37) arylamino groups such as an anilino group, naphthylamino group or anthranylamino group; (38) aralkylamino groups such as a benzylamino group or phenethylamino group; (39) alkylsulfonylamino groups such as a methylsulfonylamino group, ethylsulfonylamino group, n-propylsulfonylamino group, i-propylsulfonylamino group or n-butylsulfonylamino group; (40) arylsulfonylamino groups such as a phenylsulfonylamino group;

(41) heteroarylsulfonylamino groups such as a piperazinylsulfonylamino group; (42) acylamino groups such as a formylamino group, acetylamino group, propanoylamino group, butyrylamino group, i-propylcarbonylamino group or benzoylamino group; (43) alkoxycarbonylamino groups such as a methoxycarbonylamino group or ethoxycarbonylamino group; (44) haloalkylsulfonylamino groups such as a fluoromethylsulfonylamino group, chloromethylsulfonylamino group, bromomethylsulfonylamino group, difluoromethylsulfonylamino group, dichloromethylsulfonylamino group, 1,1-difluoroethylsulfonylamino group, trifluoromethylsulfonylamino group, 2,2,2-trifluoroethylsulfonylamino group or pentafluoroethyl sulfonyl amino group; (45) bis(alkylsulfonyl)amino groups such as a bis(methylsulfonyl)amino group, bis(ethylsulfonyl)amino group, (ethylsulfonyl)(methylsulfonyl)amino group, bis(n-propylsulfonyl)amino group, bis(i-propylsulfonyl)amino group, bis(n-butylsulfonyl)amino group or bis(t-butylsulfonyl)amino group;

(46) bis(haloalkylsulfonyl)amino groups such as a bis(fluoromethylsulfonyl)amino group, bis(chloromethylsulfonyl)amino group, bis(bromomethylsulfonyl)amino group, bis(dichloromethylsulfonyl)amino group, bis(1,1-difluoroethylsulfonyl)amino group, bis(trifluoromethylsulfonyl)amino group, bis(2,2,2-trifluoroethylsulfonyl)amino group or bis(pentafluoroethylsulfonyl)amino group; (47) optionally substituted hydrazino groups such as a hydrazino group, N'-phenylhydrazino group, N'-methoxycarbonylhydrazino group, N'-acetylhydrazino group or N'-methylhydrazino group; (48) optionally substituted aminocarbonyl groups such as an aminocarbonyl group, dimethylaminocarbonyl group, phenylaminocarbonyl group or N-phenyl-N-methylaminocarbonyl group; (49) optionally substituted hydrazinocarbonyl groups such as a hydrazinocarbonyl group, N'-methylhydrazinocarbonyl group or N'-phenylhydrazinocarbonyl group; (50) optionally substituted iminoalkyl groups such as an N-methyliminomethyl group, 1-N-phenyliminoethyl group, N-hydroxyiminomethyl group or N-methoxyiminomethyl group;

(51) thiol groups; (52) isothiocyanato groups; (53) thiocyanato groups; (54) alkylthio groups such as a methylthio group, ethylthio group, n-propylthio group, isopropylthio group, n-butylthio group, isobutylthio group, s-butylthio group or t-butylthio group; (55) alkenylthio groups such as a vinylthio group or allylthio group; (56) alkynylthio groups such as an ethynylthio group or propargylthio group; (57) arylthio groups such as a phenylthio group or naphthylthio group; (58) heteroarylthio groups such as a 2-piridylthio group or 3-pyridazylthio group; (59) aralkylthio groups such as a benzylthio group or phenethylthio group; (60) heteroarylalkylthio groups such as a 2-pyridylmethylthio group or 2-furylmethylthio group; (61) alkylthiocarbonyl groups such as a methylthiocarbonyl group, ethylthiocarbonyl group, n-propylthiocarbonyl group, isopropylthiocarbonyl group, n-butylthiocarbonyl group, isobutylthiocarbonyl group, s-butylthiocarbonyl group or t-butylthiocarbonyl group;

(62) alkylthioalkyl groups such as a methylthiomethyl group or 1-methylthioethyl group; (63) arylthioalkyl groups such as a phenylthiomethyl group or 1-phenylthioethyl group; (64) alkylthioalkoxy groups such as a methylthiomethoxy group or 1-methylthioethoxy group; (65) arylthioalkoxy groups such as a phenylthiomethoxy group or 1-phenylthioethoxy group; (66) alkylsulfinyl groups such as a methylsulfinyl group, ethylsulfinyl group or t-butylsulfinyl group; (67) alkenylsulfinyl groups such as an allylsulfinyl group; (68) alkynylsulfinyl groups such as a propargylsulfinyl group; (69) arylsulfinyl groups such as a phenylsulfinyl group; (70) heteroarylsulfinyl groups such as a 2-pyridylsulfinyl group or 3-pyridylsulfinyl group; (71) aralkylsulfinyl groups such as a benzylsulfinyl group or phenethylsulfinyl group; (72) heteroarylalkylsulfinyl groups such as a 2-pyridylmethylsulfinyl group or 3-pyridylmethylsulfinyl group;

(73) alkylsulfonyl groups such as a methylsulfonyl group, ethylsulfonyl group or t-butylsulfonyl group; (74) alkenylsulfonyl groups such as an allylsulfonyl group; (75) alkynylsulfonyl groups such as a propargylsulfonyl group; (76) arylsulfonyl groups such as a phenylsulfonyl group; (77) heteroarylsulfonyl groups such as a 2-pyridylsulfonyl group or 3-pyridylsulfonyl group; (78) aralkylsulfonyl groups such as a benzylsulfonyl group or phenethylsulfonyl group; (79) heteroarylalkylsulfonyl groups such as a 2-pyridylmethylsulfonyl group or 3-pyridylmethylsulfonyl group; (80) unsaturated heterocyclic 5-membered ring groups such as a furan-2-yl group, furan-3-yl group, thiophen-2-yl group, thiophen-3-yl group, pyrrol-2-yl group, pyrrol-3-yl group, oxazol-2-yl group, oxazol-4-yl group, oxazol-5-yl group, thiazol-2-yl group, thiazol-4-yl group, thiazol-5-yl group, isoxazol-3-yl group, isoxazol-4-yl group, isoxazol-5-yl group, isothiazol-3-yl group, isothiazol-4-yl group, isothiazol-5-yl group, imidazol-2-yl group, imidazol-4-yl group, imidazol-5-yl group, pyrazol-3-yl group, pyrazol-4-yl group, pyrazol-5-yl group, 1,3,4-oxadiazol-2-yl group, 1,3,4-thiadiazol-2-yl group, 1,2,3-triazol-4-yl group, 1,2,4-triazol-3-yl group or 1,2,4-triazol-5-yl group;

(81) unsaturated heterocyclic 6-membered ring groups such as a pyridin-2-yl group, pyridin-3-yl group, pyridin-4-yl group, 5-chloro-3-pyridyl group, 3-trifluoromethyl-2-pyridyl group, pyridazin-3-yl group, pyridazin-4-yl group, pyrazin-2-yl group, pyrimidin-5-yl group, 1,3,5-triazin-2-yl group or 1,2,4-triazin-3-yl group; (82) saturated or partially unsaturated heterocyclic groups such as a tetrahydrofuran-2-yl group, tetrahydropyran-4-yl group, piperidin-3-yl group, pyrrolidin-2-yl group, morpholino group, piperidino group, N-methylpiperazino group or oxazolin-2-yl group; (83) heterocyclooxy groups such as a 2-pyridyloxy group or 3-isoxazolyloxy group; (84) heteroarylalkyl groups such as a 2-pyridylmethyl group or 3-pyridylmethyl group; (85) heteroarylalkoxy groups such as a 2-pyridylmethoxy group or 3-pyridylmethoxy group. These substituents exemplified in (1) to (85) above may also have substituents exemplified in (1) to (85) as long as it is chemically acceptable.

Examples of the substituted aryl group include a 4-fluorophenyl group, 4-chlorophenyl group, 2,4-dichlorophenyl group, 3,4-dichlorophenyl group, 3,5-dichlorophenyl group, 2,6-difluorophenyl group, 4-trifluoromethyl phenyl group, 4-methoxyphenyl group, 3,4-dimethoxyphenyl group, 3,4-methylene dioxyphenyl group, 4-trifluoromethoxyphenyl group, 4-methoxy-1-naphthyl group and the like.

Among these groups, A is preferably a halogen atom.

In formula (I), n represents an integer of 0 to 5, preferably an integer of 0 to 3, more preferably O. In addition, when n is 2 or more, plural A may be the same or different from each other.

In formula (I), Y represents an alkyl group. Examples of the alkyl group include a methyl group, ethyl group, n-propyl group, i-propyl group, n-butyl group, i-butyl group, s-butyl group, t-butyl group, n-pentyl group, n-hexyl group and the like. Among these groups, Y is preferably an alkyl group having 1 to 3 carbon atoms, and more preferably a methyl group.

Examples of the halogenating agent include a single chlorine (molecular chlorine), single bromine (molecular bromine), single iodine (molecular iodine), N-chlorosuccinimide, N-bromosuccinimide, phosphorus pentachloride, phosphoryl chloride, phosphorus oxychloride, thionyl chloride, phosgene, Oxalyl chloride, hypochlorite salts, hypobromite salts, cyanuric chloride, 2-chloro-1,3-dimethyl benzimidazolium-chloride, bis(2,4,6-trimethylpyridine)bromonium hexafluorophosphate, bis(2,4,6-trimethylpyridine)iodonium hexafluorophosphate, 1,3-dialkyl-2-halogenoimidazolinium halides such as 1,3-dialkyl-2-chloroimidazolinium chloride or the like; 2-chloro-1,3-dimethylbenzimidazolium chloride; combination of tetrahalocarbon and $P(R1)_3$. In addition, R1 represents an alkyl group or aryl group. Among these examples, phosgene, oxalyl chloride and phosphorus oxychloride are particularly preferable.

The amount of halogenating agent to be used is usually within a range from 1.0 to 3.0 mol, and preferably from 1.5 to 2.5 mol with respect to mol of the ketoamide derivative represented by formula (I). The solvent may be unnecessary if an excessive amount of halogenating agent is used.

The halogenation reaction is usually conducted either without a solvent, or within a solvent.

There are no particular limitations on the solvent, provided that it is an inert solvent for the halogenation reaction. Examples of the solvent include ester-based solvents such as ethyl acetate, isopropyl acetate and n-butyl acetate; ketone-based solvents such as acetone, methyl ethyl ketone, methyl isobutyl ketone and cyclohexanone; saturated hydrocarbon-based solvents such as n-pentane, n-hexane, cyclohexane, methylcyclohexane and n-heptane; nitrile-based solvents such as acetonitrile and benzonitrile; ether-based solvents such as diethyl ether, diisopropyl ether, dioxane, tetrahydrofuran and 1,2-dimethoxyethane; sulfur-containing solvents such as dimethyl sulfoxide and sulfolane; amide-based solvents such as N,N-dimethylformamide, N,N-dimethylacetamide and hexamethylphosphoramide; halogenated hydrocarbon-based solvents such as methylene chloride, chloroform, carbon tetrachloride and 1,2-dichloroethane; and aromatic hydrocarbon-based solvents such as benzene, toluene and monochlorobenzene. These solvents may be used individually or in combinations containing two or more different solvents. Among these solvents, halogenated hydrocarbon-based solvents or aromatic hydrocarbon-based solvents are preferable, and chloroform, methylene chloride or benzene is more preferable.

In those cases where a solvent is used, the amount of the solvent is usually within a range from 0.001 to 100 parts by mass per 1 part by mass of the ketoamide derivative represented by formula (I).

The reaction temperature is normally 0° C. to a solvent reflux temperature, preferably 10° C. to 50° C. Although the reaction time varies according to the reaction scale, it is normally 30 minutes to 12 hours.

Following completion of the reaction, typical post-processing operations or product purification may be performed. There are no particular limitations on the purification method, and conventional methods such as distillation, recrystallization or column chromatography may be used. In addition, the solvent recovered by a solvent evaporation may be reused.

According to the above-described method, the imidoyl halide derivative represented by formula (II) can be obtained. In addition, in formula (II), A, n and Y are as defined above, X represents a halogen atom.

II. Production of 1-alkyl-5-benzoyl-1H-tetrazole Derivative Represented by Formula (IV)

Next, the imidoyl halide derivative represented by formula (II) is reacted with the azide represented by formula (III).

In formula (III), M represents an alkali metal or alkali earth metal, m represents 1 or 2.

Examples of azide represented by formula (III) include an azide of alkali metal such as sodium, potassium or the like; or an azide of alkali earth metal such as calcium, magnesium or the like. Among these examples, an azide of alkali metal is preferable, and a sodium azide is more preferable.

The amount of azide represented by formula (III) to be used is preferably 1.0 to 4.0 mol, and more preferably 1.1 to 3.0 mol with respect to 1 mol of imidoyl halide derivative.

The reaction between the imidoyl halide derivative represented by formula (II) and the azide represented by formula (III) is usually performed in a solvent. The solvent is preferably a polar solvent or an aromatic hydrocarbon solvent.

Examples of the polar solvent include N,N-dimethyl formamide, N,N-dimethyl acetamide, N-methyl formanilide, acetonitrile, tetrahydrofuran and the like. Among these examples, N,N-dimethyl formamide, acetonitrile, tetrahydrofuran are preferable.

Examples of the aromatic hydrocarbon solvent include benzene, toluene, xylene, mesitylene, ethyl benzene, chlorobenzene, nitrobenzene, cumene, chlorotoluene and the like. Among these examples, toluene, xylene are preferable.

The amount of solvent to be used is preferably 1 to 15 ml, and more preferably 3 to 10 ml with respect to 1 g of the imidoyl halide derivative represented by formula (II).

When using the aromatic hydrocarbon solvent, it is necessary to use an amine salt together with the aromatic hydrocarbon solvent. Examples of the amine salt include a primary amine salt such as methylamine salt, ethylamine salt, propylamine salt, butylamine salt, amylamine salt, hexylamine salt, cyclohexylamine salt, heptylamine salt, octylamine salt, allylamine salt, benzylamine salt, a-phenyl ethylamine salt, β-phenyl ethylamine salt or the like; secondary amine salt such as dimethylamine salt, diethylamine salt, dipropylamine salt, dibutylamine salt, diamylamine salt, dihexylamine salt, dicyclohexylamine salt, diallylamine salt, morpholine salt, piperidine salt, hexamethylene imine salt or the like; tertiary amine salt such as trimethylamine salt, triethylamine salt, tripropylamine salt, tributylamine salt, triamylamine salt, trihexylamine salt, triallylamine salt, pyridine salt, triethanolamine salt, N-methyl morpholine salt, N,N-dimethyl cyclohexylamine salt, N,N-dimethyl aniline salt, N,N,N',N'-tetramethyl ethylene diamine salt, 4-dimethyl aminopyridine salt or the like; and the like. Two or more of the amine salts may be used in combination.

Examples of the acid forming a salt include an inorganic acid such as hydrochloric acid, hydrobromic acid, sulfuric acid, nitric acid, phosphoric acid, boric acid, hydrogen azide, chloric acid, carbonic acid, hydrogen sulfide or the like; an organic acid such as formic acid, acetic acid, trifluoroacetic acid, propionic acid, oxalic acid, methane sulfonic acid, benzene sulfonic acid, toluene sulfonic acid or the like; and the like. The amount of amine salt to be used is preferably 0.1 to 1.5 mol, and more preferably 0.3 to 1.0 mol with respect to 1 mol of the imidoyl halide derivative represented by formula (II).

The reaction temperature is preferably 0 to 150° C., and more preferably 20 to 100° C., because if the reaction temperature is too low, the reaction rate is reduced, and if the reaction temperature is too high, by-product is increased. In addition, although the reaction time depends on the reaction scale, it is preferably 1 to 48 hours, and more preferably 1 to 24 hours.

Following completion of the reaction, the reaction may be stopped by cooling the reaction system to room temperature and adding water. The additive amount of water is preferably 2 to 15 ml, and more preferably 2 to 10 ml with respect to 1 g of the imidoyl halide derivative represented by formula (II). Next, the crude residue may be obtained by known means such as liquid separation, dehumidification, filtration, solvent evaporation or the like. In addition, the 1-alkyl-5-benzoyl-1H-tetrazole derivative represented by formula (IV) may be obtained by purification such as crystallization, recrystallization, or column chromatography or the like. The solvent recovered by solvent evaporation may be reused. In addition, in formula (IV), A, n and Y are as defined above.

In addition, the tetrazolyl hydroxyimino derivative represented by formula (V) may be easily produced by reacting the 1-alkyl-5-benzoyl-1H-tetrazole derivative represented by formula (IV) with a hydroxylamine or salt thereof The 1-alkyl-5-benzoyl-1H-tetrazole derivative represented by formula (IV) obtained by the process for preparation of the present invention is also useful as an intermediate for producing a plant disease control agent or the like.

For example, the tetrazolyl oxime derivative represented by formula (1-a) can be produced from the 1-alkyl-5-benzoyl-1H-tetrazole derivative represented by formula (IV) and the tetrazolyl hydroxyimino derivative represented by formula (V).

III. Production of Tetrazolyl Oxime Derivative and Salt Thereof

As described above, the tetrazolyl oxime derivative represented by formula (1-a) may be produced by reacting the 1-alkyl-5-benzoyl-1H-tetrazole derivative represented by formula (IV) obtained by the process for preparation of the present invention with the hydroxylamine to obtain the tetrazolyl hydroxyimino derivative represented by formula (V), followed by reacting the tetrazolyl hydroxyimino derivative with the Het-CH2L (provided that L represents a chlorine atom, bromine atom or iodine atom) in the presence of the base. In addition, in formula (1-a), A represents a halogen atom, alkyl group, haloalkyl group, alkoxy group, haloalkoxy group, alkyl sulfonyl group, optionally substituted aryl group, cyano group or nitro group; n represents an integer of 0 to 5 (when n is 2 or more, plural A may be the same or different from each other); Y represents an alkyl group; Het represents a substituted pyridyl group or a substituted thiazolyl group.

Examples of the base to be used in this reaction include inorganic bases such as sodium hydroxide, potassium hydroxide, sodium hydride, sodium carbonate, potassium carbonate or the like; organic bases such as triethylamine, 4-(dimethylamino)pyridine, pyridine, 1,8-diazabicyclo[5.4.0]undecene-7,1,5-diazabicyclo[4.3.0]nonene-5; and the like. One type of these bases can be used alone or two or more types can be used in combination.

The amount of base to be used is normally 0.01 to 100 times mol, and preferably 0.1 to 5 times mol with respect to the tetrazolyl hydroxyimino derivative represented by formula (V).

This reaction can be carried out in the presence or absence of a solvent.

There are no particular limitations on the solvent to be used provided that it is an inert solvent in the reaction. Examples of solvents include hydrocarbon-based solvents such as pentane, hexane, heptane, benzene, toluene or xylene; halogen-based solvents such as dichloromethane, chloroform, carbon tetrachloride; nitrile-based solvents such as acetonitrile or propionitrile; ether-based solvents such as diethyl ether, dioxane or tetrahydrofuran; amide-based solvents such as N,N-dimethylformamide, N,N-dimethylacetamide or N-methylpyrrolidone; sulfoxide-based solvents such as dimethylsulfoxide; water; and mixed solvents thereof The temperature during the reaction is normally −70 to +200° C., and preferably −20 to +100° C. Although the reaction time varies according to the reaction scale or the like, it is normally within the range of 30 minutes to 24 hours.

In addition, the salt of the compound represented by formula (1-a) may be produced by causing an acid to act upon the compound represented by formula (1-a) according to a conventional method.

The substituent of the substituted pyridyl group or the substituted thiazolyl group, which is represented by Het, may be substituted with a chemically-acceptable group according to known chemical reaction.

In the tetrazolyl oxime derivative represented by the aforementioned formula (1), there exist (E)-form and (Z)-form stereoisomers based on a carbon-nitrogen double bond of oxime moiety. Synthetic products are normally obtained in the (Z)-form only or as a mixture of the (E)-form and (Z)-form. The two isomers can be respectively isolated from a mixture of the (E)-form and (Z)-form by separating in accordance with known techniques such as silica gel column chromatography. Both the (Z)-form and (E)-form have activity, and the (Z)-form is preferable.

There are no particular limitations on the salt of the tetrazolyl oxime derivative represented by formula (1-a) provided that they are agriculturally and horticulturally acceptable salts. Examples of the salt include salts of inorganic acids such as hydrochlorides, nitrates, sulfates phosphates or the like; and salts of organic acids such as acetates, lactates, propionates, benzoates or the like.

With respect to whichever reaction, the target compound represented by formula (1-a) and the salt thereof may be isolated by performing a normal post-processing operation after termination of the reaction. In addition, if purification of the product is required, a purification means known to those skilled in the art such as distillation, recrystallization, or column chromatography or the like may be applied.

IV. Plant Disease Control Agent

The tetrazolyl oxime derivative represented by formula (1-a) or salt thereof has superior antimicrobial effects against a wide spectrum of types of mold fungi such as Oomycetes species, Ascomycetes species, Deuteromycetes species and Basidiomycetes species.

Thus, a composition having as an active ingredient thereof the tetrazolyl oxime derivative represented by formula (1-a) or salt thereof can be used to control various plant diseases occurring during cultivation of agricultural and horticultural crops such as flowering plants, grasses and forage grasses by seed treatment, foliar spraying, soil application or paddy water application and the like.

In addition, various pathogens have recently developed resistance to phenylamide fungicides and strobilurin fungicides resulting in inadequate efficacy of these fungicides, thereby creating the need for effective fungicides against resistant organisms as well. The tetrazolyl oxime derivative represented by formula (1-a) or salt thereof also have superior antimicrobial effects against resistant organisms in addition to pathogens that are sensitive to these fungicides.

The tetrazolyl oxime derivative represented by formula (1-a) or salt thereof can also be used as anti-fouling agents for preventing aquatic organisms from adhering to boat bottoms, fishing nets and other objects in contact with water.

In addition, some intermediate compounds produced in the process for preparation of the tetrazolyl oxime derivative represented by formula (1-a) or salt thereof also demonstrate antimicrobial activity.

Moreover, the tetrazolyl oxime derivative represented by formula (1-a) or salt thereof can also be used as antimicrobial or anti-mold agents for walls, bathtubs, shoes or clothing by incorporating in paint or fibers and the like.

The plant disease control agent containing as an active ingredient thereof the tetrazolyl oxime derivative represented by formula (1-1) or salt thereof may adopt a form containing only the tetrazolyl oxime derivative represented by formula (1-a) or salt thereof, or may adopt a form able to be adopted by ordinary agricultural chemicals, namely a wettable powder, granules, powder, emulsion, aqueous solution, suspension or flowable agent.

Although the amount of active ingredient in the preparations is not particularly limited, normally, it is 0.5 to 95% by mass, and preferably 2 to 70% by mass based on the total amount of the composition (preparation).

Although the plant disease control agent containing as an active ingredient thereof the tetrazolyl oxime derivative represented by formula (1-a) or salt thereof is naturally adequately effective even if used alone, it can also be used by mixing with fungicides, insecticides, miticides or synergists.

EXAMPLE

The present invention will be explained in more detail by way of Examples, but the present invention should not be interpreted to be limited to these Examples.

Example 1

Production of 5-benzoyl-1-methyltetrazole 36.5 L of methanol and 12 kg (73 mol) of a compound represented by formula (Oa) were placed in a reactor provided with a stirrer, reflux apparatus and a dropping funnel, and 87.6 mol of methylamine was added to the reactor while controlling the temperature to 15 to 20° C. The reaction was performed for 5 hours. 11.79 kg of a compound represented by formula (Ia) was obtained by this reaction. The yield was 95.4%.

The compound represented by formula (Ia) obtained in the above-described reaction was added to 73 L of chloroform, and 109.5 mol of thionyl chloride was added while controlling the temperature to 15 to 20° C. The reaction was performed for 1 hour and performed for another 6.5 hours at the temperature of solvent reflux temperature. 23 kg (including solvent) of the compound represented by formula (IIa) was obtained by this reaction.

Next, the compound represented by formula (IIa) was added to 65.7 L of acetonitrile, and 87.6 mol of sodium azide was added to the resulting reaction solution while controlling the temperature to 9 to 27° C. The reaction was performed for 12 hours. The compound represented by formula (Iva) was obtained by this reaction. The yield was 62.5%.

7.5 kg of the compound represented by formula (Iva) was added to 79.8 L of ethanol, and 79.8 mol of hydroxylamine hydrochloride was added to the resulting solution while controlling the temperature to 45 to 50° C. The reaction was performed for 7 hours. The compound represented by formula (Va) was obtained by this reaction. The ratio between the Z-form and E-form was 94.3:5.7. The yield was 93%.

[Chemical formula 11]

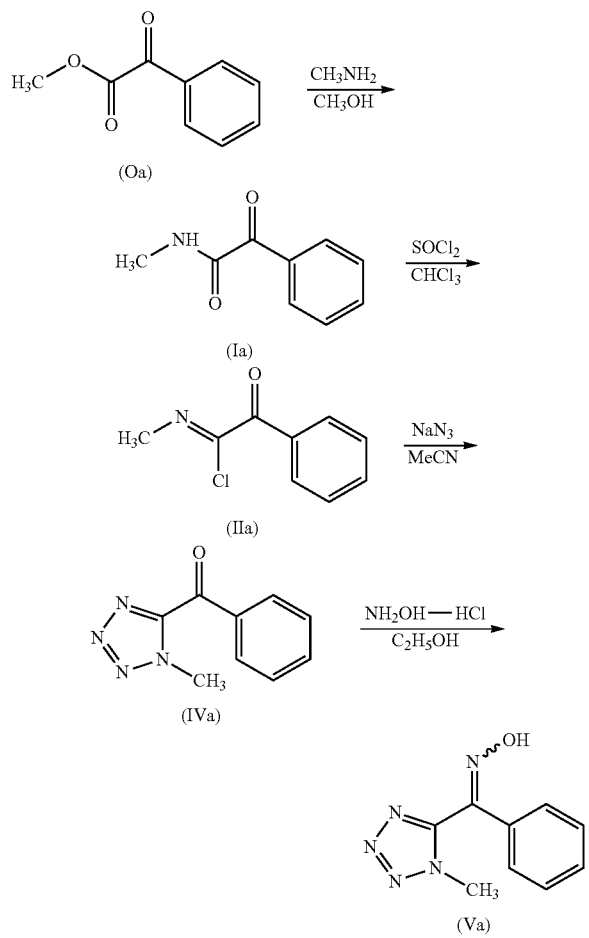

INDUSTRIAL APPLICABILITY

According to the present invention, a tetrazolyl oxime derivative having a superior plant disease control effect can be produced using as a starting material thereof a ketoamide derivative that is relatively easy to produce and access, thereby making it industrially useful.

The invention claimed is:

1. A process for preparation of 1-alkyl-5-benzoyl-1H-tetrazole derivative comprising:
   a step 1 of reacting a ketoamide derivative represented by formula (I):

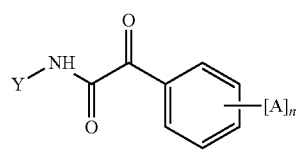

(in formula (I), A represents a halogen atom, alkyl group, haloalkyl group, alkoxy group, haloalkoxy group, alkyl sulfonyl group, optionally substituted aryl group, cyano group or nitro group; n represents an integer of 0 to 5 (when n is 2 or more, plural A may be the same or different from each other);

Y represents an alkyl group) with a halogenating agent to obtain an imidoyl halide derivative represented by formula (II):

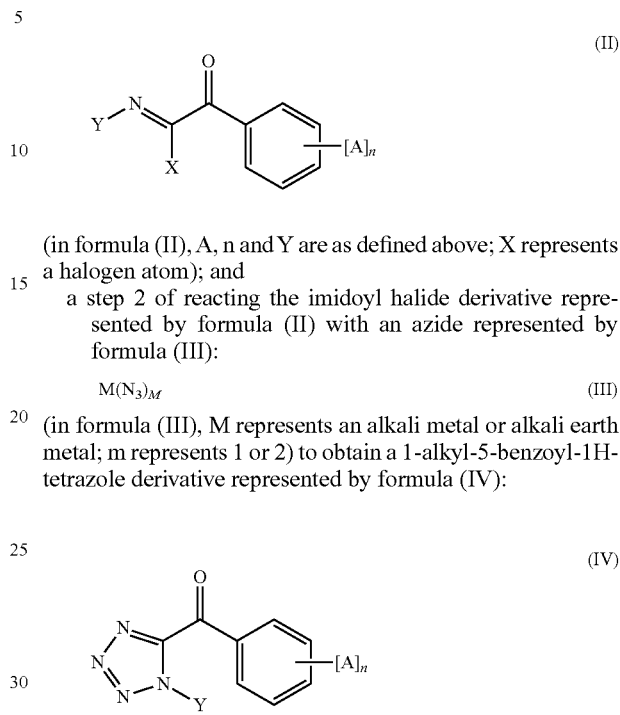

(in formula (II), A, n and Y are as defined above; X represents a halogen atom); and
   a step 2 of reacting the imidoyl halide derivative represented by formula (II) with an azide represented by formula (III):

$$M(N_3)_M \qquad (III)$$

(in formula (III), M represents an alkali metal or alkali earth metal; m represents 1 or 2) to obtain a 1-alkyl-5-benzoyl-1H-tetrazole derivative represented by formula (IV):

(IV)

(image of formula IV)

(in formula (IV), A, n and Y are as defined above).

2. The process for preparation of 1-alkyl-5-benzoyl-1H-tetrazole derivative according to claim 1, wherein
   in the step 1, the halogenating agent is at least one selected from the group consisting of phosgene, oxalyl chloride, thionyl chloride and phosphorus oxychloride.

3. The process for preparation of 1-alkyl-5-benzoyl-1H-tetrazole derivative according to claim 1, wherein
   in the step 2, the azide represented by formula (III) is sodium azide.

4. The process for preparation of 1-alkyl-5-benzoyl-1H-tetrazole derivative according to claim 1, wherein
   in the step 1, chloroform, methylene chloride or benzene is used as a solvent.

5. A process for preparation of tetrazolyl hydroxyimino comprising:
   causing a hydroxylamine or salt thereof to act upon the 1-alkyl-5-benzoyl-1H-tetrazole derivative obtained by the process for preparation according to any one of claims 1 to 4 to obtain a tetrazolyl hydroxyimino derivative represented by formula (V):

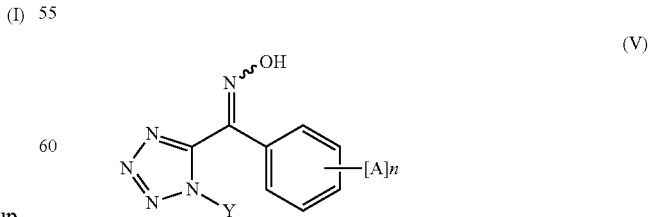

(in formula (V), A, n and Y are as defined above).

* * * * *

UNITED STATES PATENT AND TRADEMARK OFFICE
CERTIFICATE OF CORRECTION

PATENT NO.         : 8,273,781 B2
APPLICATION NO.    : 13/255345
DATED              : September 25, 2012
INVENTOR(S)        : Suzuki et al.

It is certified that error appears in the above-identified patent and that said Letters Patent is hereby corrected as shown below:

Column 4, Formula (III): change "$M(N_3)_M$" to -- $M(N_3)_m$ --.

Column 11, Line 41: change "a-phenyl" to -- α-phenyl --.

Column 13, Line 7: change "thereof" to -- thereof. --.

Column 14, Line 13: change "(1-1)" to -- (1-a) --.

Column 14, Line 59: change "(Iva)" to -- (IVa) --.

Column 14, Line 61: change "(Iva)" to -- (IVa) --.

Column 16, Formula (III): change "$M(N_3)_M$" to -- $M(N_3)_m$ --.

Signed and Sealed this
Twelfth Day of March, 2013

Teresa Stanek Rea
*Acting Director of the United States Patent and Trademark Office*